United States Patent
Lee et al.

(10) Patent No.: US 9,526,683 B2
(45) Date of Patent: Dec. 27, 2016

(54) INORGANIC COMPOSITE POWDER COATED WITH OCTYL METHOXYCINNAMATE, AND ULTRAVIOLET BLOCKING COSMETIC COMPOSITION USING SAME

(75) Inventors: Beom Zoo Lee, Gyeonggi-do (KR); Seung Woo Lee, Gyeonggi-do (KR); Soon Kyu Jeong, Gyeonggi-do (KR); Do Yeun Kim, Seoul (KR); Hyung Ran Kwak, Gyeonggi-do (KR)

(73) Assignee: CHEMLAND. CO., LTD, Pyeongtaek (KR)

( * ) Notice: Subject to any disclaimer, the term of this patent is extended or adjusted under 35 U.S.C. 154(b) by 0 days.

(21) Appl. No.: 14/117,992

(22) PCT Filed: May 18, 2012

(86) PCT No.: PCT/KR2012/003951
§ 371 (c)(1),
(2), (4) Date: Nov. 15, 2013

(87) PCT Pub. No.: WO2012/157993
PCT Pub. Date: Nov. 22, 2012

(65) Prior Publication Data
US 2015/0132392 A1   May 14, 2015

(30) Foreign Application Priority Data
May 18, 2011   (KR) .................. 10-2011-0047049

(51) Int. Cl.
*A61Q 17/04*   (2006.01)
*A61K 8/37*   (2006.01)
(Continued)

(52) U.S. Cl.
CPC ............. *A61K 8/37* (2013.01); *A61K 8/022* (2013.01); *A61K 8/0241* (2013.01); *A61K 8/19* (2013.01);
(Continued)

(58) Field of Classification Search
None
See application file for complete search history.

(56) References Cited

U.S. PATENT DOCUMENTS

2004/0247543 A1* 12/2004 Huerta ............. A61K 8/27
  424/59
2007/0160549 A1*  7/2007 Hunt et al. ............ 424/59

FOREIGN PATENT DOCUMENTS

EP   1402883 A1 *  3/2004
JP   04-198124 A    7/1992
(Continued)

OTHER PUBLICATIONS

JN Israelachvili, S Marcelja, RG Horn. "Physical Principles of Membrane Organization." Quarterly Reviews of Biophysics, vol. 13 (2), 1980, pp. 121-200.*
(Continued)

*Primary Examiner* — Isaac Shomer
(74) *Attorney, Agent, or Firm* — STIP Law Group, LLC

(57) ABSTRACT

Disclosed is an inorganic composite powder containing an inorganic ultraviolet filter, and a method for preparing the same. The present invention also relates to an SPF and PA which can be employed in the preparation of the inorganic composite powder using Octyl Methoxycinnamate (OMC) without loss of the OMC in the range of 0.1 to 60% and which have superior ultraviolet blocking effects.

4 Claims, 3 Drawing Sheets

(51) Int. Cl.
  *A61K 8/29* (2006.01)
  *A61K 8/55* (2006.01)
  *A61K 8/02* (2006.01)
  *A61K 8/19* (2006.01)
(52) U.S. Cl.
  CPC ............... *A61K 8/29* (2013.01); *A61K 8/553* (2013.01); *A61Q 17/04* (2013.01); *A61K 2800/612* (2013.01)

(56) References Cited

FOREIGN PATENT DOCUMENTS

| | | | | |
|---|---|---|---|---|
| JP | 04-198124 A | * | 7/1992 | ............... A61K 7/42 |
| JP | 11-043626 A | | 2/1999 | |
| KR | 10-20020010736 A | | 2/2002 | |
| KR | 10-20080051830 A | | 6/2008 | |
| KR | 10-20090069370 A | | 7/2009 | |
| KR | 10-2009-010851 A | | 10/2009 | |
| KR | 10-0966362 B1 | | 6/2010 | |
| KR | 1020110001537 | | 1/2011 | |

OTHER PUBLICATIONS

Machine Translation of KR 1020110001537, published May 7, 2012. Translation obtained from http://engpat.kipris.or.kr/pmt/patent/getTransRes.do?commKey=null&AN=1020090059105&PK=B0102&MA=K2E&FROM=EN&NATION=KR on Oct. 26, 2016, pp. 1-18.*

* cited by examiner

INORGANIC COMPOSITE POWDER COATED WITH OCTYL METHOXYCINNAMATE, AND ULTRAVIOLET BLOCKING COSMETIC COMPOSITION USING SAME

CROSS-REFERENCE TO RELATED APPLICATION

This application claims the benefit of Korean Patent Application No. 10-2011-0047049, filed on May 18, 2011 in the Korean Intellectual Property Office, the disclosure of which is incorporated herein by reference.

TECHNICAL FIELD

The present invention relates to an inorganic composite powder coated with octyl methoxycinnamate, and an ultraviolet blocking cosmetic composition using the same.

BACKGROUND

Recently, as a destruction of an ozone layer is intensifying together with a rapid environmental pollution, an adverse effect on human health by an ultraviolet (UV) light is also increasing, and thus it is urgent to establish measures for this. UV light is a major factor that causes pigmentation and various pigmented skin disease, and can give rise to a direct impact on an intracellular pigment-producing function to increase the deposition of melanin pigment and can cause freckles and age spots.

In general, UV light means a light having a wavelength of 200~400 nm in sunlight, and covers about 6% of sunlight reaching a surface of an earth. Depending on a wavelength range and length by UV light, a wavelength in the range of 320~400 nm is classified as UV-A, a wavelength in the range of 280~320 nm is classified as UV-B, a wavelength in the range of 200~280 nm is classified as UV-C, and a light covering 90% or more of the ultraviolet light reaching the surface of the earth is UV-A. Since UV-A has a long wavelength, it is easily penetrated into a deep place of a skin compared to other UVs having different range such as B and C, and thus, causes an immediate tanning after lapse of 1~2 hours, and also since the wavelength of UV-B is short compared to that of UV-A, UV-B causes a sun burn. Although UV-C is the shortest UV light among the UV lights and does not reach the surface of the earth since it is absorbed by an ozone layer located on a stratosphere, UV-C reaching the surface of the earth is also increasing due to the destruction of the ozone layer as mentioned above, and thus it is urgent to establish measures for this. A short wavelength of UV-C is a direct factor causing a skin cancer, because it has energy much larger than a kinetic energy that molecules of a cell have and thus breaks a molecular bond of DNA, etc.

Sunscreen (agent) or ultraviolet blocking agent used in cosmetics is largely classified into an organic-based UV absorbent (organic UV filter) and an inorganic-based UV scattering agent (physical UV filter).

The organic UV absorber is a compound having a conjugated double bond in a molecule, when it absorbs UV light, it becomes an excited state due to an increase of an electronic energy in a molecule, but immediately emits a heat and fluorescence and then returns a ground state. An absorption wavelength or coefficient, etc. of such UV absorber is changed according to a structure of a product, and mostly absorbs UV-B region. Generally, the compound commonly used as raw material of UV absorbent is Octyl Methoxycinnamate of a family of cinnamic acid, which is represented by a Formula [I] as below:

Formula I

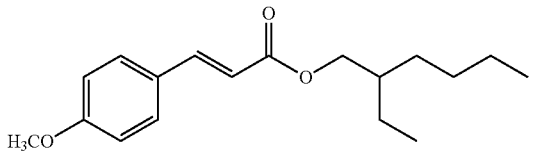

The compound as described above is a representative organic-based UV absorbent, and since it has an excellent compatibility with silicone oil and can be combined easily with other materials, it is widely used in general.

In addition, a representative ultraviolet light absorber absorbing UV-A region is Butyl Methoxydibenzoylmethane and comprises an aromatic compound having a conjugated double-bond represented by the below Formula [II], like OMC (Octyl Methoxycinnamate). Since it is a raw material having very good blocking effect for UV-A region, when it is used with only small amounts in a formulation, the UV blocking effect can be identified:

Formula 2

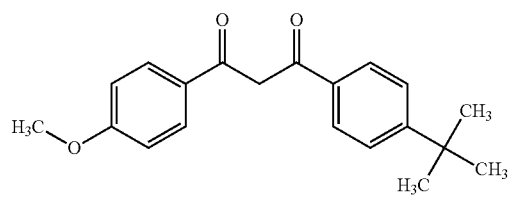

On the other hand, an UV scattering agent has a characteristic that it can widely block UV-A and -B regions, with a specificity for a wavelength more than an organic UV absorber. The inorganic UV scattering agent includes Titanium Dioxide, Zinc Oxide, etc., and has a relatively high safety compared to the organic UV absorber.

An organic UV absorber literally has a characteristic of absorbing an ultraviolet light, while an inorganic UV scattering agent has an ultraviolet screening effect by blocking and scattering ultraviolet light. That is, the materials mentioned above are metal salts having a high refractive index, and since they have a high degree of surface reflection for an ultraviolet light, they can effectively scatter the ultraviolet light. Inorganic materials widely used as the inorganic UV scattering agent are illustrated in the below Table 1.

TABLE 1

Refractive index of an inorganic UV scattering agent

| Material | Refractive index |
| --- | --- |
| Titanium Dioxide (Rutile) | 2.7 |
| Titanium Dioxide (Anatase) | 2.5 |
| Chromium oxide | 2.5 |
| Iron oxide | 2.4 |
| Zirconium oxide | 2.2 |
| Zinc oxide | 1.9 |
| Alumina | 1.8 |

TABLE 1-continued

Refractive index of an inorganic UV scattering agent

| Material | Refractive index |
| --- | --- |
| Talc | 1.6 |
| Kaoline | 1.6 |
| Water | 1.3 |

In addition, the benefits of such inorganic UV scattering agent are that it has no ultraviolet light screening-lowering effect as time lapses, there are fewer legal restrictions in a limitation for combination than an organic UV absorber, and a safety for a human body is high. Also, the wavelength range which can absorb UV light is broad.

Such inorganic UV scattering agents were used as those having a relatively large particle size (1 μm or less) in the past, but since the material having a large particle size causes the white residue on the skin and is reduced in UV-blocking effect, an ultra-fine inorganic material having a small particle size (0.1 μm or less) is preferred at present. Since the material does not cause the white residue on the skin upon applying to a formulation, and also effectively blocks the UV light range more than a visible light, it is commonly used in sunscreen products.

Sun protection factor (SPF) is an index for representing a blocking effect for UV-B, and is a value for determining as to how long a product can expose a skin to sunlight without causing an erythema phenomenon for the skin. SPF is a value obtained with dividing a minimum erythema dose obtained on the area of skin that are applied with a sunscreen product by a minimum erythema dose obtained with an irradiation of UV-B on the area of skin that are not applied with the sunscreen product, and is represented as below:

$$SPF = \frac{\text{A Minimum erythema dose of a skin applying a sunscreen product } (MED)}{\text{A Minimum erythema dose of a skin not applying a sunscreen product } (MED)}$$

Meanwhile, the Talc refers to a raw stone, is generally a designation, but at present, a crushed power is named as the inorganic powder. Since the Talc has characteristics of a low hardness, high whiteness and low electrical conductivity, it exhibits characteristics of the chemical and thermal inactivation. The Talc is used in a variety of Industrial fields such as a paper manufacture, medicine manufacture, etc., and is commonly used as a main base material in a make-up powder cosmetic in the field of cosmetics.

Recently, there has been a social issue due to detection of asbestos-containing Talc in a product such as baby powder, etc., and thus, a powder make-up cosmetic to which the Talc is not added is being developed by many companies. However, since it has not been known up to now for raw materials in which characteristics such as applicabilities of the Talc to a skin and a press pressure on the powder formulation, etc., can be entirely replaced, the Talc in the powder cosmetics covers a considerable portion.

The Talc for cosmetics is a clay mineral having a formula of $Mg_3Si_4O_{10}(OH)_2$, and has a layer-like structure positioning a magnesium layer on two (2) silica layers as in a structural model III as shown below. Since an interlayer coupling is predominated by Van der waals force, a binding force is weak more than other minerals. Major producers of the Talc are China, Australia, USA, Korea, France, Italia, etc., and there are differences in quality of the Talc according to a place of origin.

Formula 3

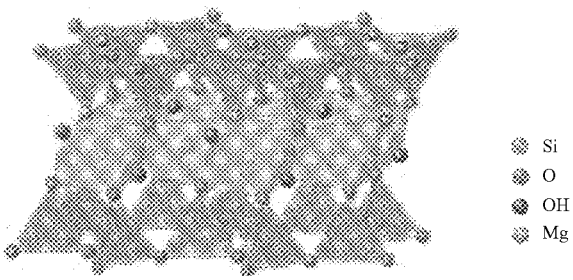

Talc is a hydrated magnesium silicate whose chemical formula is $Mg_3Si_4O_{10}(OH)_2$

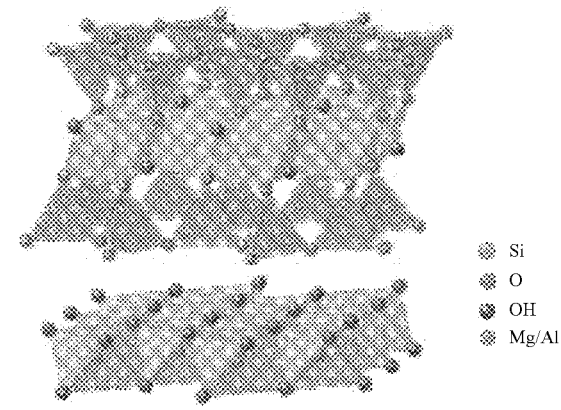

Chlorite is a hydrated magnesium aluminium silicate whose chemical formula is $(Mg_{6-x-y}Fe_yAl_x)(Si_{4-x}Al_y)O_{10}(OH)_8$.

Since such the Talc has a refractive index lower than a white pigment such as titanium oxide and zinc oxide and has a small difference in the refractive index with water or oil, it maintains the state of being transparent or translucent in such media, and thus a hiding (shielding) power is small or less.

Disclosure

Accordingly, the purpose of the present invention resides in preparing an inorganic composite powder that has an ability of blocking UV light by coating Octyl Methoxycinnamate on an inorganic powder, and providing a cosmetic composition blocking UV light by applying the inorganic composite powder to powder cosmetics.

In order to achieve the purpose, the present invention provides a novel cosmetic composition useful for blocking UV light by deciding an optimal coating concentration of an organic UV absorbent, OMC, and using an inorganic composite powder wherein 10% OMC is coated.

Technical Solution

The purpose of the present invention was achieved by a step of preparing Octyl Methoxycinnamate (OMC) base which is an organic UV absorber; and a step of preparing the OMC-containing inorganic composite powder, and also a step of surface-treatment of the OMC on an inorganic plate powder with different concentrations to identify the coating or not; a step of measuring sun protection factor for coating powder and identifying an optimal concentration of OMC to the inorganic powder; a step of making a formulation by using the inorganic composite powder which the coating concentration of OMC is determined; and a step of comparing and estimating the sun protection factors (SPF) between the formulation used inorganic composite powder and an existing sunscreen products.

Advantageous Effect

The present invention has an excellent effect in providing a novel cosmetic composition useful for blocking an ultra-violet by deciding an optimal coating concentration of an organic UV absorber, OMC, and using an inorganic composite powder which 10% OMC is coated.

BRIEF DESCRIPTION OF THE DRAWINGS

The above and other features of the present invention will now be described in detail with reference to certain exemplary embodiments thereof illustrated the accompanying drawings which are given herein below by way of illustration only, and thus are not limitative of the present invention, and wherein.

BEST MODE FOR THE INVENTION

Hereinafter, the concrete constitutions of the present invention are illustrated in detail by means of Examples.

The inorganic powder of the present invention comprises an talc.

Embodiment

Preparation of an Inorganic Composite Powder Coated with OMC

Figure 1:
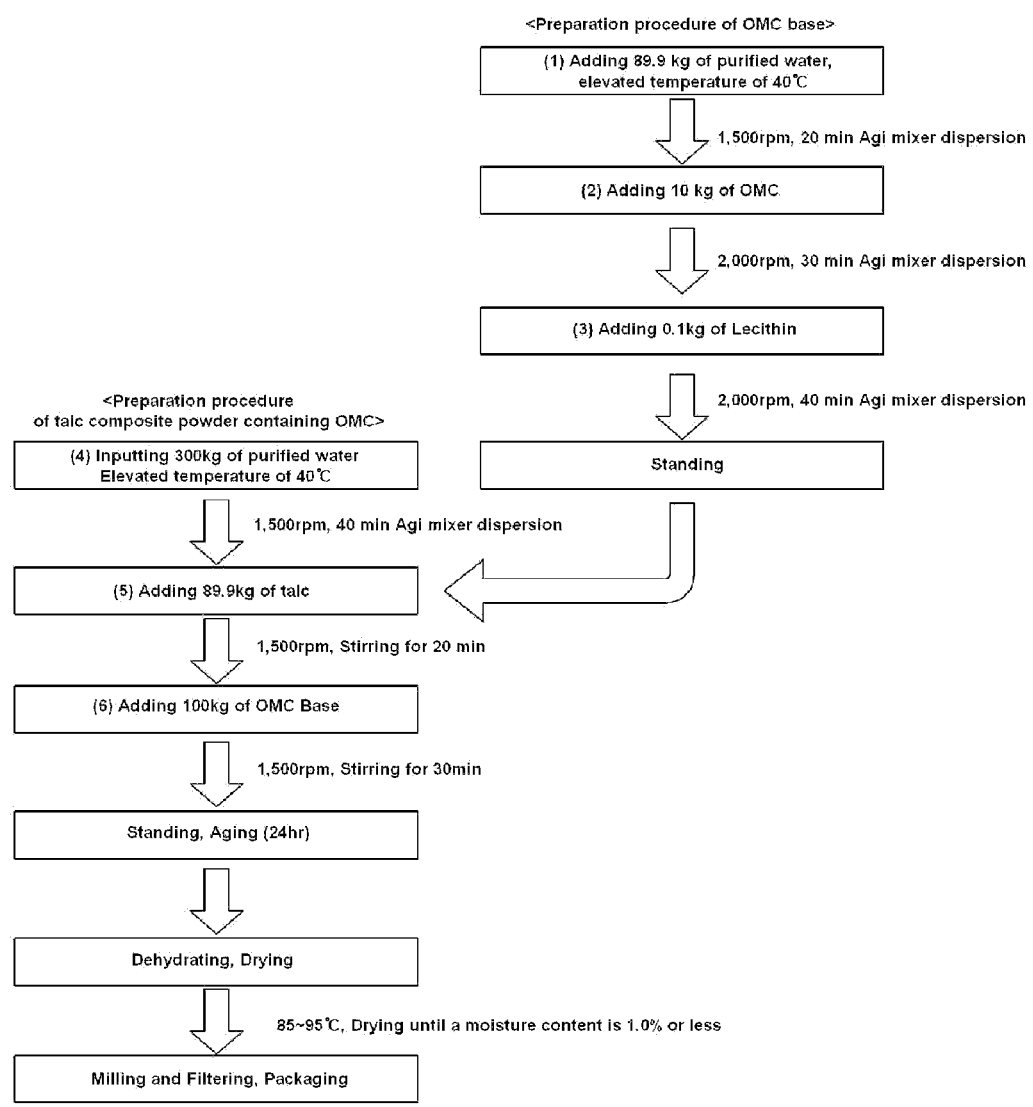
FIG. 1 is a preparation flow chart of an inorganic composite powder coated with OMC according to the present invention.

A preparation of the inorganic composite powder coated with OMC according to the present invention is accomplished by firstly preparing OMC base and then adding it to an inorganic powder (FIG. 1). However, this is no more than an exemplification of the example, and it is self-evident that simple modifications of the above are also included in the technical scope of the present invention.

In order to produce 100 kg of the inorganic composite powder, 10 kg of OMC is added into 89.9 kg of DI water (Deionized water) having a temperature of 40° C., stirred for 20 min at 1,500 rpm, and vigorously stirred for 30 min at an increased 2,000 rpm again, and then 0.1 kg of Lecithin is added and vigorously stirred and dispersed for 40 min at the same speed to prepare 100.0 kg of OMC base and then was let to stand to age.

In order to produce an inorganic composite powder having an inorganic material with OMC base prepared from the above, separately from this, 300 kg of DI water was raised to 40° C. and 89.9 kg of an inorganic powder was added while stirring the DI water was stirred at 1,500 rpm, and stirred for 20 min at 1,500 rpm, and 100 kg of OMC base prepared from the above was added, and stirred it for 30 min at the same speed, and then was let to stand to age for 24 hrs.

After dehydrating OMC base-containing inorganic composite powder. It is dried at 85~95° C. until the moisture content is 1% or less, and is filtered with 100~200 mesh of a vibration sieve to mill, and then the product other than notified materials is packaged and commercialized.

The content ratios of the materials used in OMC base preparation and the OMC base containing inorganic composite powder preparation of the present invention were 10% OMC and 89.9% inorganic powder and 0.1% Lecithin.

The preferable temperature for dispersing the OMC, inorganic powder and Lecithin which are the raw materials in the present invention was identified as being 35~45° C., and the stirring speed of the stirrer was 1,000 rpm~2,500 rpm, preferably 1,500 rpm~2,000 rpm in particular upon dispersing.

Experimental Example 1

Identification of Actual Coating Amount According to OMC Coating Concentration

An identification of a coating amount in the present experiment was performed at Korea Testing & Research Institute, and an equipment used necessary for an analysis was US EPA 3550C, 2007 (HPLC). OMC concentrations used in the powder coating were applied as 5, 10, 15 and 20%, the contents of OMC coated on the inorganic powder by HPLC analysis are as shown in Table 2 as below;

TABLE 2

| OMC content coated on actual inorganic powder according to OMC surface- coating concentration (% by weight) ||
|---|---|
| OMC surface-treating concentration (%) | Actual coated OMC content (%) |
| 5.0 | 5.1 |
| 10.0 | 10.2 |
| 15.0 | 12.9 |
| 20.0 | 18.2 |

Figure 2:
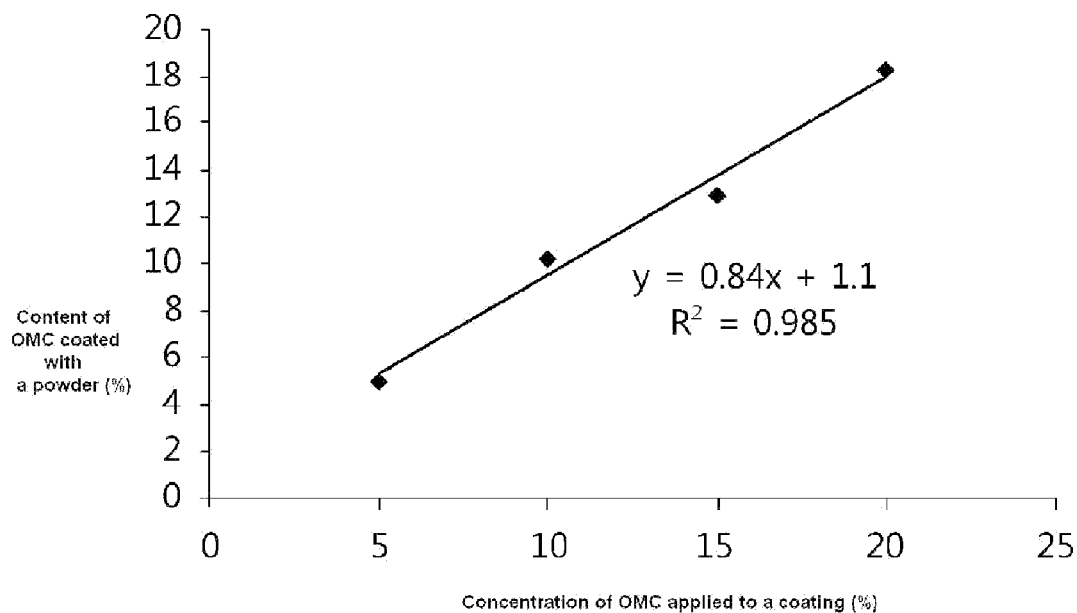
FIG. 2 is a graph showing OMC quantitative value coated on actual inorganic powder depending on OMC applying concentration according to the present invention.

On the basis of the experimental results, the correlation for quantitative amount of actual coating according to the surface-treating concentration is shown in FIG. 2. As can be identified from the FIG., a positive (+) correlation between actual coated contents depending on OMC surface-treating concentration was established, and the value of $R^2$ was identified significantly as being 0.985.

Experimental Example 2

Identification of Loss or not During Coating Procedure

The present experiment is to identify the amount of OMC lost via experimental loss during a coating procedure, was performed at Korea Testing & Research Institute by using the same equipment as the Experimental Example 1, and the contents of OMC lost during the coating procedure are as shown in Table 3.

TABLE 3

OMC contents lost during coating procedure in OMC-containing composite powder coated with concentrations different from each other

| OMC coating concentration (%) | OMC content lost during coating (mg/kg) |
|---|---|
| 5.0 | 258 |
| 10.0 | Not Detected |
| 15.0 | Not Detected |
| 20.0 | Not Detected |

[note] * Analysis Institution: Korea Testing & Research Institute
* Testing Method: US EPA 3550C: 2007 (HPLC)
* Method Detection Limit (MDL): 5.0 mg/kg As identified from the experimental results, the sample in which the loss of OMC during the coating procedure was identified was that when the concentration was 5% OMC, and if the coating concentration was increased to 10~20%, the loss of OMC during the coating procedure was not identified. From the present experimental results, it was identified that most nearly of OMC applied to the experiment was coated to the inorganic powder.

Experimental Example 3

Sun Protection Factor and PA Value Quantitative Amount According to OMC Coating Content by Each of Concentrations In the present example, sun protection factor was identified by measuring SPF and PA values for the inorganic composite powder which was surface-treated with the different concentrations of OMC, and the results are shown in Table 4 as below.

TABLE 4

SPF and PA values for the inorganic composite powder coated with the different concentrations of OMC.

| OMC applying concentration | SPF | PA |
|---|---|---|
| 0* | 2 | 1 |
| 5.0 | 12 | 5 |
| 10.0 | 15 | 17 |
| 15.0 | 15 | 22 |
| 20.0 | 16 | 26 |

[note]
*Raw materials of inorganic powder not coated with OMC
SPF, PA analyzing equipment: Optometries SPF-290S Analyzer Upon identifying SPF and PA values depending on the concentrations of OMC as shown in Table 4 as above, in the case of PA they are increased in proportion to OMC coating concentration, but SPF was represented as nearly similar values in the case of OMC applying concentrations of 10, 15 and 20%. A correlation between OMC coating concentration and sun protection factor was identified, and the results on this are represented in FIG. 3.

Figure 3:
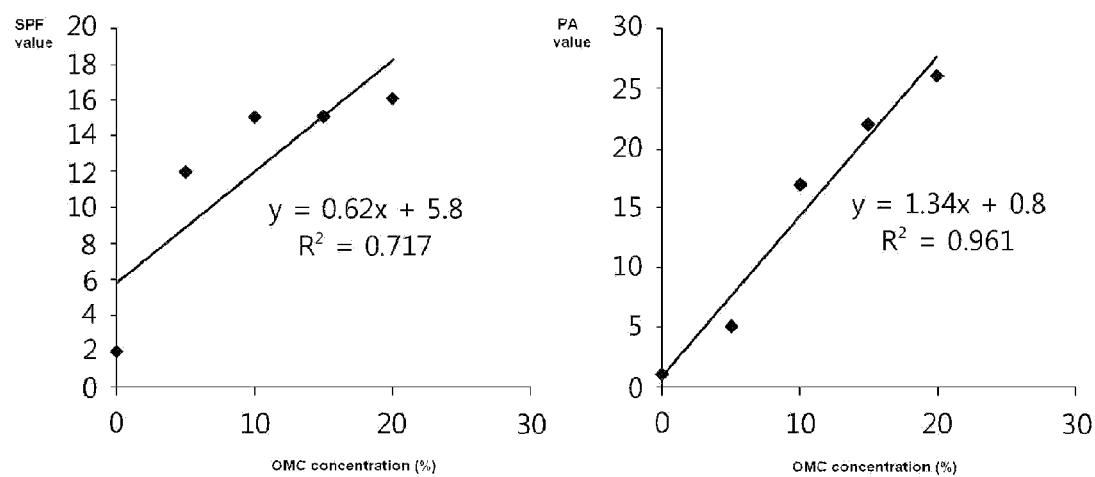
FIG. 3 is a graph showing a correlation between SPF and PA values depending on OMC coating concentration of the present invention.

As seen from FIG. 3, since SPF value was not increased with the large width at 10% or more of OMC concentration, 10% is identified as being the most effective OMC concentration in the coating of the present invention. On the other hand, PA was increased in proportion to the coating concentration of OMC.

From the results identified via the present experiment, it was identified that the best concentration of OMC coating to the inorganic powder is 10%, and 10% OMC-containing inorganic composite powder was applied to the formulation experiment of the present invention, but it is fine if 0.1~60.0% of OMC is used when preparing the actual inorganic composite powder and cosmetics of the present invention.

Experimental Example 4

Identification of SPF Value in Powder Cosmetics Applied with Talc OMC (10%)

In the present experiment, a loose powder was prepared by using the inorganic composite powder that 10% of OMC was surface-treated on the basis of the research results previously practiced, and sun protection factor for this was identified. Further, in order to identify the extent of the ultraviolet protection in the loose powder formulation to which the present raw material is applied, a separate formulation as a control was prepared. Also, the difference between two formulations different from each other, one to which inorganic composite powder 10% OMC coated was applied, and the other which the same amount of OMC used as a binder, was identified.

The prescriptions for the formulation samples different from each other are shown in Table 5, and SPF value between the samples prepared by this prescription is shown in FIG. 3.

TABLE 5

Prescription for formulation samples for identifying sun protection factor

|   | INCI Name | Sample a[1] | Sample b[2] | Sample c[3] |
|---|---|---|---|---|
| A | Talc/Magnesium Stearate | 55.07 | 55.07 | 36.5 |
|   | Talc/Ethylhexyl Methoxycinnmate | 0 | 0 | 55.0 |
|   | Talc/Titanium Dioxide/ Triethoxycaprylylsilane | 31.0 | 31.0 | 0 |
|   | Polymethylmethacrylate crosspolymer | 6.0 | 6.0 | 6.07 |
|   | Titanium Dioxide/ Triethoxycaprylylsilane | 1.0 | 1.0 | 1.0 |
| B | Iron oxide yellow/ Triethoxycaprylylsilane | 0.38 | 0.38 | 0.38 |
|   | Iron oxide black/ Triethoxycaprylylsilane | 0.69 | 0.69 | 0.69 |
|   | Iron oxide red/Triethoxycaprylylsilane | 0.06 | 0.06 | 0.06 |
| C | Propyl parahydroxybenzoate | 0.1 | 0.1 | 0.1 |
|   | Methyl parahydroxybenzoate | 0.2 | 0.2 | 0.2 |
|   | Diethylhexyl Maleate | 5.5 | 0 | 0 |
|   | Ethylhexyl Methoxycinnamate | 0 | 5.5 | 0 |
|   | Total | 100 | 100 | 100 |

[note]
[1]Prescription which any OMC is not added (OMC content 0%)
[2]Containing OMC as a binder (OMC content 5.5%)
[3]Inorganic composite powder which coated with OMC is added (OMC content 5.5%)

Figure 4:
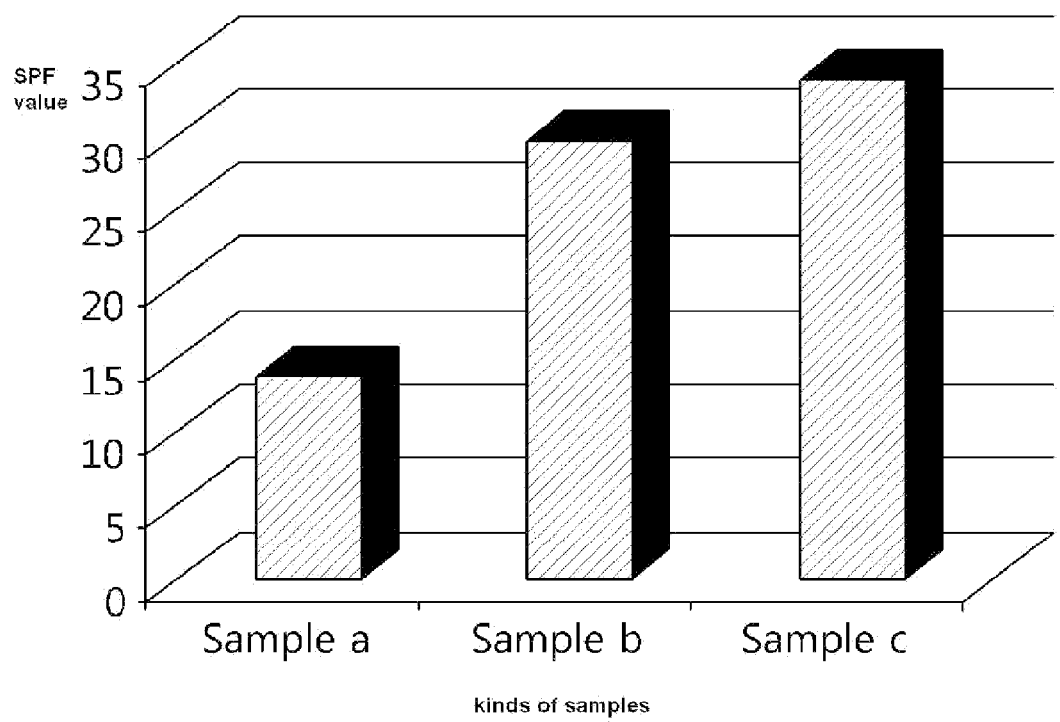
FIG. 4 is a picture showing sun protection factors between formulations different from each other according to the present invention.

As identified in FIG. 4, the value of sun protection factor for 3 kinds of formulation samples showed the difference which is different from each other. Sample (a) is a formulation to which OMC is not added, and was used as a control for other formulations. Although the same amount of OMC was applied to the formulations in the sample b and sample c, a higher sun protection factor was measured in the formulation that the inorganic composite powder OMC was coated, compared to the formulation to which OMC was added as a general binder.

This was decided that in the case that OMC is sprayed in the form of binder the amount covered on the surface of the powder is not uniform, whereas since the inorganic composite powder coated with OMC is already uniformly coated on the surface of the inorganic powder, when the equivalent amount was applied to the same formulation, a higher sun protection factor was obtained.

INDUSTRIAL APPLICABILITY

The present invention has excellent effects providing cosmetics useful for blocking ultraviolet light by using a formulation to which a composite powder coated with OMC is applied, by coating OMC as an organic UV absorber to inorganic powder with different concentrations to determine an optimal coating concentration which can impart an efficient sun protection factor, and identifying the sun protection factor upon applying the composite powder wherein the coating concentration is determined to the formulation (ex. loose powder), and thus, is very useful in the functional cosmetics industries.

What is claimed is:

1. An inorganic composite powder for blocking ultraviolet light, comprising 10% Octyl Methoxycinnamate, 89.9% inorganic powder and 0.1% Lecithin.

2. An inorganic composite powder for blocking ultraviolet light, comprising 10% Octyl Methoxycinnamate, 89.9% inorganic powder and 0.1% Lecithin, wherein the inorganic composite powder is prepared by a preparation method comprising:
   a) a step of dispersing Octyl Methoxycinnamate (OMC) and Lecithin in DI water having a temperature of 35~45° C.;
   b) separately from the step a), a step of dispersing the inorganic powder in DI water having the temperature of 35~45° C.;
   c) a step of adding the dispersion of the step a) to the dispersion of the step b) and then stirring and dispersing it;
   d) a step of aging the dispersion of step c) for 24 hours;
   e) a step of dehydrating and drying it so that a moisture content thereof is 1% or less at the temperature of 85~95° C.; and
   f) a step of milling and filtering it with 100~200 mesh of a vibration sieve.

3. A cosmetic composition for blocking ultraviolet light, which comprises the composite powder of claim 2 as an effective component.

4. A method for preparing an inorganic composite powder for blocking ultraviolet light, which comprises:
   a) a step of dispersing Octyl Methoxycinnamate (OMC) and Lecithin in deionized (DI) water having a temperature of 35-45° C.;
   b) separately from the step a), a step of dispersing the inorganic powder in DI water having the temperature of 35-45° C.;
   c) a step of adding the dispersion of the step a) to the dispersion of the step b) and then stirring and dispersing it;
   d) a step of aging the dispersion of step c) for 24 hours;
   e) a step of dehydrating and drying it so that a moisture content thereof is 1% or less at the temperature of 85-95° C.; and
   f) a step of milling and filtering it with 100-200 mesh of a vibration sieve.

* * * * *